(12) United States Patent
Burnier et al.

(10) Patent No.: US 6,488,941 B1
(45) Date of Patent: Dec. 3, 2002

(54) OIL-IN-WATER EMULSIONS CONTAINING HIGH WAX CONTENT AND A SOFTPASTE OILY PHASE

(75) Inventors: Veronique Burnier, Paris (FR); Veronique Roulier, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/459,990

(22) Filed: Dec. 14, 1999

(30) Foreign Application Priority Data

Dec. 14, 1998 (FR) .............................. 98 15763

(51) Int. Cl.$^7$ ................................. A61K 6/00
(52) U.S. Cl. ...................... 424/401; 424/63; 424/64; 424/70.19; 424/70.31; 424/78.03; 514/937; 514/938; 514/943; 514/772; 514/787; 514/788.1
(58) Field of Search ............... 424/401, 70.19, 424/70.31, 78.03; 514/937, 938, 943, 772, 787

(56) References Cited

U.S. PATENT DOCUMENTS

| | | | | |
|---|---|---|---|---|
| 4,788,001 A | * | 11/1988 | Narula | 252/312 |
| 5,665,687 A | | 9/1997 | Khayat et al. | 510/136 |
| 5,723,137 A | * | 3/1998 | Wahle et al. | 424/401 |
| 5,897,869 A | * | 4/1999 | Roulier et al. | 424/401 |

FOREIGN PATENT DOCUMENTS

| | | |
|---|---|---|
| DE | 43 37 041 A1 | 5/1995 |
| FR | 0 667 146 A1 | 8/1995 |
| FR | 0 705 593 A1 | 4/1996 |
| FR | 0 815 846 A1 | 1/1998 |
| FR | 0 835 651 A2 | 4/1998 |

OTHER PUBLICATIONS

U.S. patent application Ser. No. 09/459,990, filed Dec. 14, 1999, pending.
U.S. patent application Ser. No. 09/453,470, filed Dec. 02, 1999, pending.
U.S. patent application Ser. No. 09/451,918, filed Dec. 01, 1999, pending.

* cited by examiner

Primary Examiner—Thurman K. Page
Assistant Examiner—Lakshmi Channavajjala
(74) Attorney, Agent, or Firm—Oblon, Spivak, McClelland, Maier & Neustadt, P.C.

(57) ABSTRACT

A composition in the form of an oil-in-water (o/w) emulsion containing an oily phase dispersed in an aqueous phase, which contains a mixture of nonionic emulsifiers, the mixture being liquid at ambient temperature and having an HLB ranging from about 6 to 13, and in that the oily phase comprises at least about 5% by weight of one or more waxes based on the total weight of the composition, at least one of the waxes having a starting melting temperature of greater than or equal to about 50° C.

25 Claims, No Drawings

OIL-IN-WATER EMULSIONS CONTAINING HIGH WAX CONTENT AND A SOFTPASTE OILY PHASE

BACKGROUND OF THE INVENTION

1. Field of the Invention

The present invention relates to a composition in the form of an oil-in-water (O/W) emulsion containing a high content of wax and to the use thereof in the cosmetics and dermatological fields, in particular in caring for, treating and/or making up the skin and/or mucous membranes, and more particularly in the treatment of wrinkles and/or fine lines of the skin and/or in the treatment and/or protection of dry skin.

The invention also relates to a process for the preparation of such a composition, wherein at least one stage of the process is carried out using a mixer-extruder.

2. Discussion of the Background

It is known to use waxes in cosmetic creams in the form of emulsions and which are used in the care of human skin, and, in particular, for the antiwrinkle effects contributed by these waxes. Nevertheless, it is difficult to incorporate a high percentage of waxes in these compositions because waxes have a tendency to greatly thicken emulsions. In addition, when a high percentage of waxes is incorporated in an emulsion, the emulsion is very difficult to apply to the skin because it does not slip. Furthermore, a rough effect is produced on the skin. Such an emulsion is therefore of no practical use.

Furthermore, it is also known to incorporate a high percentage of waxes in mascaras. However, compositions of this type cannot be used as a care product because of the above-mentioned disadvantages.

Furthermore, in order to prepare an emulsion containing waxes, it is necessary to melt the waxes in the fatty phase of the emulsion, and in particular if it is desired, for example, to use waxes, such as carnauba waxes, which are particularly advantageous because of their antiwrinkle effect on the skin. In so doing, it is therefore necessary to heat the fatty phase to 80–85° C., which is particularly harmful when it is desired to introduce heat-sensitive compounds thereto.

A need therefore remains for a composition containing a significant percentage of waxes without the above disadvantages.

SUMMARY OF THE INVENTION

Accordingly, it is an object of the present invention to provide an O/W emulsion having a high wax content therein.

It is also an object of the present invention to provide a process for preparing an O/W emulsion having a high wax content therein.

It is, moreover, an object of the present invention to provide a method of treating mammalian skin, mucous membranes and/or hair using an o/w emulsion having a high wax content therein.

The above object and others are provided by a composition in the form of an oil-in-water (O/W) emulsion, containing an oily phase dispersed in an aqueous phase, which contains a mixture of at least two nonionic emulsifiers, the mixture being liquid at ambient temperature and having an HLB ranging from about 6 to 13, and wherein the oily phase contains at least about 5% by weight of one or more waxes based on the total weight of the composition, at least one of the waxes having a starting melting temperature of greater than or equal to about 50° C.

DETAILED DESCRIPTION OF THE PREFERRED EMBODIMENTS

Quite surprisingly, it has now been discovered, in accordance with the present invention, that it is possible to incorporate a high percentage of waxes in O/W emulsions, while retaining satisfactory fluidity and a pleasant feeling during application on the skin, by preparing the emulsion under cold conditions using a mixture of nonionic emulsifiers, which is liquid at ambient temperature and which has an appropriate HLB (HLB=Hydrophilic Lipophilic Balance), and starting from a soft oily phase containing a high percentage of waxes.

The present invention thus provides a composition in the form of an oil-in-water emulsion containing an oily phase dispersed in an aqueous phase, which contains a mixture of at least two nonionic emulsifiers, the mixture being liquid at ambient temperature and having an HLB ranging from about 6 to 13, and wherein the oily phase contains at least about 5% by weight of one or more waxes based on the total weight of the composition, at least one of the waxes being a wax having a starting melting temperature of greater than or equal to about 50° C.

The composition obtained, although containing a high level of wax, is fresh on application.

The present inventors have particularly sought to avoid the use of ionic emulsifiers, which can be irritating to some skin types, notably to sensitive skin. However, the use of nonionic emulsifiers presents difficulties as there exists no nonionic emulsifier which is liquid at ambient temperature and which has an HLB ranging from about 6 to 13 which makes it possible to achieve the purpose and effect of the prevent invention. The present inventors have surprisingly discovered the effectiveness of using a mixture of nonionic emulsifiers.

The mixture of nonionic emulsifiers which is used in accordance with the present invention must be liquid at ambient temperature, that is to say at a temperature ranging from about 15° C. to 25° C., and have an HLB ranging from about 6 about to 13. It can contain in particular (1) at least one nonionic emulsifier having an HLB equal to or greater than about 13, and (2) at least one nonionic emulsifier having an HLB equal to or less than about 5. In addition, it can optionally contain at least one coemulsifier which may in particular be necessary if the emulsifiers (1) and (2) used are both solids, the coemulsifier then being liquid and making it possible to obtain a liquid mixture.

As is known, the HLB of a mixture of emulsifiers corresponds to the mean of the HLB values of each of the emulsifiers constituting the mixture, taking into account the proportion by weight of these emulsifiers.

Mention may be made, as nonionic emulsifiers with an HLB equal to or less than 5, of, for example, esters of polyols and of a fatty acid having an alkyl chain containing from 12 to 22 carbon atoms, such as esters of fatty acid and of glycerol, of glucose or of sorbitol; oxyethylenated derivatives of esters of polyols and of a fatty acid having an alkyl chain containing from 12 to 22 carbon atoms, which derivatives contain from 1 to 50 oxyethylene groups, such as a complex of triisostearin (triester of glycerol and of isostearic acid) and of PEG-6; ethers of polyethylene glycol and of a fatty alcohol having an alkyl chain containing from 12 to 22 carbon atoms, which ethers contain from 1 to 50 oxyethylene groups, such as oleyl ethers and in particular oleth-25 (25 oxyethylene groups), and their mixtures.

Use may advantageously be made, as nonionic emulsifiers with an HLB equal to or less than about 5, of those which are liquid at ambient temperature, such as polyol fatty esters and fatty ethers with a branched or unsaturated chain containing from 12 to 22 carbon atoms and, in particular, sorbitan monoisostearate, such as the product sold under the name "Arlacel 987" by the company ICI, sorbitan mono/dioleate, such as the product sold under the name "Arlacel 83" by the company ICI, the complex of triisostearin and of PEG-6, such as the product sold under the name "Labrafil isostearic" by the company Gattefossé, decaglyceryl pentaisostearate, such as the product sold under the name "Nikkol Decaglyn 5-IS" by the company Nikko Chemical, or methyl glucose dioleate, such as the product sold under the name "Isolan DO" by the company Goldschmidt.

Mention may be made, as nonionic emulsifiers with an HLB equal to or greater than about 13, of, for example, esters of polyethylene glycol and of a fatty acid having an alkyl chain containing from 12 to 22 carbon atoms, which esters contain from 5 to 100 and preferably from 20 to 60 oxyethylene groups, such as PEG-40 stearate; ethers of polyethylene glycol and of a fatty alcohol having an alkyl chain containing from 12 to 22 carbon atoms, which ethers contain from 5 to 100 and preferably from 10 to 30 oxyethylene groups, such as ceteareth-25 or ceteth-25; esters of sorbitan and of a fatty acid having an alkyl chain containing from 12 to 22 carbon atoms, which esters comprise from 0 to 100 and preferably from 4 to 25 oxyethylene groups, such as polysorbate 20, polysorbate 40 and polysorbate 60; esters of sugar and of a fatty acid having an alkyl chain containing from 12 to 22 carbon atoms, such as sucrose stearate; derivatives of polyethylene glycol and of esters of glycerol and of a fatty acid having an alkyl chain containing from 12 to 22 carbon atoms, such as PEG-8 caprylic/capric glycerides; polyethylene glycol ethers of esters of methyl glucose and of a fatty acid having an alkyl chain containing from 12 to 22 carbon atoms, such as PEG-20 methyl glucose sesquistearate; and their mixtures.

Use may advantageously be made, as nonionic emulsifiers with an HLB equal to or greater than about 13, of those which are liquid at ambient temperature, such as polysorbate 20, for example the product sold under the name "Tween 20" by the company ICI, polysorbate 40, for example the product sold under the name "Tween 40" by the company ICI, PEG-8 caprylic/capric glycerides, for example the product sold under the name "Labrasoll, by the company Gattefossé, or PEG-20 methyl glucose sesquistearate, for example the product sold under the name "Glucamate SSE 20" by the company Amerchol.

Mention may be made, as a coemulsifier, of, for example, fatty alcohols containing a branched or unsaturated chain having from 8 to 22 carbon atoms, such as isostearyl alcohol; fatty acids containing a branched or unsaturated chain having from 8 to 22 carbon atoms, such as ricinoleic acid; esters of a polyol and of a branched fatty acid containing from 8 to 22 carbon atoms, such as branched fatty esters of glycerol or of propylene glycol, for example glyceryl isostearate or propylene glycol isostearate, and their mixtures.

Mention may be made, as a mixture of nonionic emulsifiers, which is liquid at ambient temperature and which has an HLB of 6 to 13, which can be used in the composition according to the invention, of, for example, the mixture of glyceryl stearate, propylene glycol stearate, glyceryl isostearate, propylene glycol isostearate, oleth-25 and ceteth-25 sold by the company Gattefossé under the name "Hydrolactol 70", with an HLB of 10.

The amount of mixture of emulsifiers (emulsifiers and coemulsifier) in the composition according to the invention generally ranges from about 0.1 to 30% by weight of active material, and preferably from about 1 to 25% by weight of active material with respect to the total weight of the composition. The proportion of each emulsifier in this amount of emulsifiers can be easily determined by a person skilled in the art for the purpose of obtaining a mixture suitable for the criteria defined above. Preferably, the amount of nonionic emulsifiers, without taking into account the coemulsifier, ranges from about 0.5 to 10% by weight and preferably from about 0.5 to 5% by weight with respect to the total weight of the composition.

The composition of the present invention contains, in the oily phase, at least about 5% by weight of one or more waxes with respect to the total weight of the composition. The cooled oily phase oily phase, before it is mixed with the aqueous phase, advantageously exists in the form of a soft paste. The term "soft pastel" is understood here to mean a paste for which the viscosity can be measured, in contrast to the solid structure of a tube or stick, for which the viscosity cannot be measured. The dynamic viscosity of the soft paste at 25° C. is generally between 3 and 35 Pa·s, measured with a Contraves TV rotary viscometer equipped with an "MS-r4" rotor at a frequency of 60 Hz.

Mention may be made, as waxes which can be used in the composition of the invention, of, for example, mineral waxes, such as microcrystalline waxes, paraffin wax, petrolatum wax, petroleum wax, ozokerite or montan wax; animal waxes, such as beeswax, lanolin and its derivatives; vegetable waxes, such as candelilla, ouricurry, carnauba or japan waxes, cocoa butter, or cork fibre or sugar cane waxes; hydrogenated oils which are solid at 25° C. fatty esters and glycerides which are solid at 25° C.; synthetic waxes, such as polyethylene waxes and waxes obtained by the Fischer-Tropsch synthesis; silicone waxes, and their mixtures.

According to the present invention, use is made of at least one wax having a starting melting temperature greater than or equal to about 50° C. and preferably at least one wax for which the starting melting temperature is greater than about 65° C., such as carnauba wax, some polyethylene waxes and some microcrystalline waxes, such as that sold by the company Tisco under the name "Tisco Wax 88" or that sold by the company RMC under the name of "Feruwax 30540".

The term "starting melting temperature" is understood to mean, in the present description, the temperature at which a wax begins to melt. This temperature can be determined by DTA (differential thermal analysis), which makes it possible to obtain a thermogram (or melt curve) of the wax under consideration. The starting melting temperature corresponds to the temperature at which a significant change of slope in the thermogram can be observed. The melting point, for its part, represents the minimum point in the said thermogram.

The amount of wax(es) in the composition of the invention is at least about 5% and preferably ranges from about 5 to 30%, and preferably from about 5 to 15% by weight with respect to the total weight of the composition.

The amount of oily phase in the composition of the invention generally ranges from about 10 to 70%, and preferably from about 20 to 50% by weight with respect to the total weight of the composition. This oily phase is used in such an amount or else comprises an amount of waxes such that the amount of waxes in the final composition is equal to or greater than about 5%.

The oily phase of the composition of the invention generally comprises, in addition to the wax or waxes, one or more fatty substances chosen from oils of animal origin, oils of vegetable origin, mineral oils, synthetic oils, fluorinated oils, silicone oils, in particular volatile silicone oils, silicone gums, silicone resins, fatty alcohols, fatty acids and silicone elastomers, such as the products sold under the name "KSG" by the company Shin-Etsu, under the name "Trefil", by the company Dow Corning or under the name "Gransil" by the company General Electric.

The composition according to the present invention can advantageously also contain one or more fillers (pulverulent constituents) which can be, for example, talc; micas of natural or synthetic origin; kaolin; zinc or titanium oxides; calcium carbonate; magnesium carbonate and hydrocarbonate; silica, in particular spherical silica, silica powder, sold under the name "Cab-O-Sil TS 530" by the company Cabot, and silica microbeads, such as those sold under the name SB150 by the company Myoshi; titanium dioxide; glass and ceramic beads sold by the company 3M under the trade name "Macrolite"; metal soaps derived from an organic carboxylic acid having from 8 to 22 carbon atoms, preferably from 12 to 18 carbon atoms, for example zinc, magnesium or lithium stearate, zinc laurate or magnesium myristate; powders formed from nonexpanded synthetic polymers, such as powders formed from polyethylene, polystyrene, polyesters, polyamides (for example, Nylon or poly-β-alanine), acrylate copolymers (for example, the microporous microspheres sold by the company Dow Corning under the trade name "Polytrap"), poly(methacrylic acid)s, polystyrene or teflon, such as "Fluon"; expanded powders, such as hollow microspheres made of thermoplastic material prepared by known processes, such as those disclosed in U.S. Pat. No. 3,615,972 and EP-A-056,219, and in particular the microspheres sold under the trade name "Expancel" by the company Kemanord Plast or under the trade name "Micropearl F 80 ED" by the company Matsumoto; powders formed from natural organic materials, such as maize, wheat or rice starches, which may or may not be crosslinked, such as the powders formed from starch crosslinked by octenylsuccinic anhydride sold under the name "Dry-Flo" by the company National Starch; silicone resin microbeads, such as those sold under the name "Tospearl" by the company Toshiba Silicone, and their mixtures.

The fillers can represent up to about 20% by weight with respect to the total weight of the composition and preferably from about 1 to 12% by weight with respect to the total weight of the composition.

The aqueous phase of the composition of the present invention represents at least about 30% by weight with respect to the total weight of the composition and preferably from about 50 to 80% by weight with respect to the total weight of the composition.

The composition according to the present invention can be used in any field where this type of pharmaceutical dosage form is advantageous and in particular in the cosmetics and dermatological fields. When it constitutes a cosmetic and/or dermatological composition, it advantageously contains a physiologically acceptable medium, which is to say a medium which is compatible with the skin, mucous membranes, nails and/or hair.

The compositions which are the subject-matter of the present invention are applied in a large number of treatments of the skin, mucous membranes (lips) and hair, including the scalp, in particular in protecting, caring for, cleansing and/or making up the skin and/or so mucous membranes, in protecting, caring for and/or cleansing the hair and/or in the therapeutic treatment of the skin, hair and/or mucous membranes.

The compositions according to the present invention can be used, for example, as products for treating, caring for, protecting and/or cleansing the skin, in the form of creams or milks, or as (skin and lip) make-up products by incorporating fillers and/or coloring materials (pigments and/or dyes). They are particularly appropriate in the treatment of wrinkles and/or fine lines of the skin and in the treatment and/or protection of dry skin.

The present invention also provides for the cosmetic use of the composition as defined above in treating, protecting, caring for and/or cleansing the skin, mucous membranes and/or hair and/or in making up the skin and/or mucous membranes.

The present invention also provides for the cosmetic use of the composition as defined above in treating wrinkles and/or fine lines of the skin.

The present invention also provides for the use of the composition as defined above in the manufacture of a dermatological composition intended for treating and/or protecting dry skin.

In addition, the compositions of the invention can contain adjuvants which are conventionally used in the cosmetics or dermatological field, such as hydrophilic or lipophilic active principles, preservatives, antioxidants, fragrances, solvents, sunscreen agents, coloring materials, basic or acidic agents, and lipid vesicles. These adjuvants are used in the proportions which are conventional in the cosmetics or dermatological field, for example from about 0.01 to 30% of the total weight of the composition, and they are, depending in their nature, introduced into the aqueous phase or into the oily phase of the composition or alternatively into vesicles. These adjuvants and their concentrations must be such that they do not modify the property desired for the composition.

If it is desired to obtain a less fluid composition and/or to improve the stability of the emulsion, one or more hydrophilic gelling agents, such as carboxyvinyl polymers or carbomers and polyacrylamides, can be added thereto. According to a preferred embodiment of the invention, use is made of a polyacrylamide, such as the product sold under the name Hostacerin AMPS by the company Hoechst. These gelling agents are used at concentrations ranging from about 0.05 to 2%, preferably about 0.1 to 0.5%, by weight with respect to the total weight of the composition.

Mention may be made, as active principles which can be used in the composition of the invention, of, for example, moisturizing agents, such as polyols and in particular glycerol, ethylene glycol, isoprene glycol, 1,2-propanediol, diglycerol, sorbitol, polyethylene glycols and their mixtures.

The composition according to the present invention can advantageously be prepared by using, for at least one stage of the process, a kneading device, such as a roll-mill mixer comprising two rollers rotating in opposite directions, between which the paste passes, or a screw mixer-extruder. Use is preferably made of a screw mixer-extruder.

The present invention also provides for a process for the preparation of a composition according to the present invention, whereas at least one stage of the process is carried out using a screw mixer-extruder.

According to a first embodiment, the preparation process of the present invention entails comprises the following stages:

(1) preparation of the oily phase in the form of a soft paste obtained by forming a premix of the waxes and oils, by heating this premix to a temperature at which it melts, by then introducing the molten premix. and the other constituents (in particular the fillers) of the oily phase, all at once or in several portions, into a screw mixer-extruder subject to a temperature gradient ranging from 80° C. to 20° C., and by kneading the mixture obtained while cooling it to ambient temperature as it is conveyed to the outlet of the mixer-extruder;

(2) incorporation of the mixture of emulsifiers (emulsifiers and coemulsifiers) in the soft paste obtained in (1), and (3) incorporation, with stirring, of the mixture obtained in (2) in the aqueous phase.

In this embodiment, stages (2) and (3) are carried out in a mixing device commonly used by a person skilled in the art, such as a rotor-stator.

In addition, in the process described above, the emulsifier used a mixture of nonionic emulsifiers, which is liquid at ambient temperature and which has an HLB of about 6 to 13, and the amounts used are such that the emulsion obtained comprises at least 5% of wax by weight with respect to the total weight of the composition.

As indicated above, as the mixing of the oily and aqueous phases takes place under cold conditions, the incorporation of heat-sensitive compounds is not problematic.

According to a specific embodiment of the invention, stages (2) and (3) above are also carried out in the screw mixer-extruder used for stage (1). The mixture of emulsifiers and the aqueous phase are then introduced into a part (or section) of the mixer-extruder where the temperature is close to ambient temperature.

The use of a mixer-extruder makes it possible to reproducibly obtain an oily phase paste of highly constant quality. Furthermore, it is possible, by adapting the outlet die of the mixer-extruder, to package the composition in line at the outlet of the said mixer-extruder.

The various stages of the process can be carried out in one or more extruders arranged one after the other and preferably in a single twin-screw extruder.

The conditions under which the extrusion can be carried out are known as described in FR-2515306, corresponding to U.S. Ser. No. 08/378,388, U.S. Pat. No. 6,120,781 which is incorporated herein in the entirety.

The present invention will now be further described in the following Examples which are provided solely for purposes of illustration and are not intended to be limitative. The amounts shown are percentages by weight.

EXAMPLE

Care Cream

| Oily phase | |
|---|---|
| Dry-Flo (filler) | 15% |
| Microcrystalline wax | 19% |
| Mineral oil | q.s. for 100% |
| O/W emulsion | |
| Oily phase | 30% |
| Hydrolactol 70 (mixture of emulsifiers) | 20% |
| Ammonium polyacryldimethyltauramide (Hostacerin AMPS) | 0.1% |
| Water | q.s. for 100% |

Procedure 1 i) The mixture of wax and of oil is heated to approximately 100° C., ii) the molten mixture is introduced into a mixer-extruder at the same time as the filler and the oily phase is obtained at the outlet of the mixer-extruder in the form of a soft paste, iii) the mixture of emulsifiers is incorporated in the soft paste in a rotor-stator, and iv) the mixture obtained is then added, little by little, to the aqueous phase (water and Hostacerin AMPS) while stirring.

Procedure 2 i) The mixture of wax and of oil is heated to approximately 100° C., ii) the filler is introduced into the head section of a mixer extruder comprising at least six sections, iii) the oily phase is introduced into the second section of the said screw mixer-extruder, and iv) the aqueous phase and the mixture of emulsifiers are introduced, via two different inlets, into the fourth section of the said screw mixer-extruder.

The sections of the screw mixer-extruder used are, ranging from the first to the sixth section, brought respectively to the following temperatures: 20° C., 80° C., 60° C., 20° C., 20° C. and 20° C.

A cream is obtained which exhibits a very light texture and which has good moisturizing qualities and is capable of smoothing the relief of the skin.

Having described the present invention, it will be apparent to the artisan that many changes and modifications may be made to the above-described embodiments without departing from the spirit and the scope of the present invention.

What is claimed is:

1. A composition in the form of an oil-in-water (O/W) emulsion, comprising an oily phase dispersed in an aqueous phase, which comprises a mixture of at least two nonionic emulsifiers, the mixture being liquid at ambient temperature and having an HLB ranging from about 6 to 13, and in that the oily phase comprises at least about 5% by weight of one or more waxes based on the total weight of the composition, at least one of the waxes being a wax having a starting melting temperature of greater than or equal to about 50° C., wherein the mixture of emulsifiers comprises (1) at least one nonionic emulsifier having an HLB equal to or greater than about 13, and (2) at least one nonionic emulsifier having an HLB equal to or less than 5; and wherein prior to mixing with said aqueous phase, said oily phase is in the form of a soft paste having a dynamic viscosity of between 3 and 35 Pa·s at 25° C. measured with a Contraves TV rotary viscometer equipped with an MS-r4 rotor at a frequency of 60 Hz.

2. The composition according to claim 1, wherein the mixture of emulsifiers additionally comprises at least one coemulsifier.

3. The composition according to claim 1, wherein the nonionic emulsifier having an HLB equal to or greater than about 13 comprises esters of polyethylene glycol and of a fatty acid having an alkyl chain comprising from about 12 to 22 carbon atoms, which esters comprise from about 5 to 100 oxyethylene groups; ethers of polyethylene glycol and of a fatty alcohol having an alkyl chain comprising from about 12 to 22 carbon atoms, which ethers comprise from about 5 to 100 oxyethylene groups; esters of sorbitan and of a fatty acid having an alkyl chain comprising from about 12 to 22 carbon atoms, which esters comprise from about 0 to 100 oxyethylene groups; esters of sugar and of a fatty acid having an alkyl chain comprising from about 12 to 22 carbon atoms; derivatives of polyethylene glycol and esters of glycerol and of a fatty acid having an alkyl chain comprising from about 12 to 22 carbon atoms; polyethylene glycol ethers of esters of methyl glucose and of a fatty acid having an alkyl chain comprising from about 12 to 22 carbon atoms; or mixtures thereof.

4. The composition according to claim 1, wherein the nonionic emulsifier with an HLB equal to or less than about 5 comprises esters of polyols and of fatty acids having an alkyl chain comprising from about 12 to 22 carbon atoms; oxyethylenated derivatives of esters of polyols and of a fatty acid having an alkyl chain comprising from about 12 to 22 carbon atoms, which derivatives comprise from about 1 to 50 oxyethylene groups; ethers of polyethylene glycol and of a fatty alcohol having an alkyl chain comprising from about 12 to 22 carbon atoms, which ethers comprise from about 1 to 50 oxyethylene groups, and their mixtures.

5. The composition according to claim 2, wherein the coemulsifier is chosen from the group comprising fatty alcohols comprising a branched or unsaturated chain having from about 8 to 22 carbon atoms; fatty acids comprising a branched or unsaturated chain having from about 8 to 22 carbon atoms; esters of a polyol and of a branched fatty acid comprising from about 8 to 22 carbon atoms, and their mixtures.

6. The composition according to claim 1, wherein the mixture of emulsifiers comprises glyceryl stearate, propylene glycol stearate, glyceryl isostearate, propylene glycol isostearate, oleth-25 and ceteth-25.

7. The composition according to claim 1, wherein the amount of mixture of emulsifiers ranges from 0.1 to 30% by weight of active material with respect to the total weight of the composition.

8. composition according to claim 1, wherein the wax comprises mineral waxes, animal waxes, vegetable waxes, hydrogenated oils, fatty esters and glycerides which are solid at 25° C., synthetic waxes, silicone waxes, or a mixture thereof.

9. The composition according to claim 1, wherein the wax comprises carnauba wax, polyethylene waxes having a starting melting temperature of greater than about 65° C., microcrystalline waxes having a starting melting temperature of greater than about 65° C., or a mixture thereof.

10. The composition according to claim 1, wherein the amount of wax ranges from about 5 to 30% by weight based on the total weight of the composition.

11. The composition according to claim 1, wherein the amount of oily phase ranges from about 10 to 70% by weight with respect to the total weight of the composition.

12. The composition according to claim 1, wherein the oily phase further comprises one or more fatty substances selected from the group consisting of oils of animal origin, oils of vegetable origin, mineral oils, synthetic oils, fluorinated oils, silicone oils, silicone gums, silicone resins, fatty alcohols, fatty acids and silicone elastomers.

13. The composition according to claim 1, which further comprises at least one filler.

14. The composition according to claim 13, wherein the filler is selected from the group consisting of talc, micas, kaolin, zinc and titanium oxides, calcium carbonate, magnesium carbonate and hydrocarbonate, silica, titanium dioxide, glass and ceramic beads, metal soaps, powders formed from nonexpanded synthetic polymers, expanded powders, powders formed from natural organic materials, silicone resin microbeads, and their mixtures.

15. The composition according to claim 13, wherein the amount of filler(s) ranges from about 1 to 12% by weight based on the total weight of the composition.

16. The composition according to claim 13, wherein the aqueous phase represents from about 50 to 80% by weight based the total weight of the composition.

17. The composition according to claim 13, wherein the aqueous phase comprises at least one gelling agent which is a polyacrylamide.

18. The composition according to claim 13, which is a cosmetic or dermatological composition or both.

19. A process for the preparation of a composition according to claim 1, comprising combining components of said composition to form said composition, wherein at least one stage of the process is carried out using a screw mixer-extruder.

20. The process according to claim 19, which comprises
 (1) preparing of the oily phase in the form of a soft paste obtained by forming a premix of the waxes and oils, by heating this premix to a temperature at which it melts, by then introducing the molten premix and the other constituents of the oily phase, all at once or in several portions, into a screw mixer-extruder subject to a temperature gradient ranging from about 80° C. to 20° C., and by kneading the mixture obtained while cooling it to ambient temperature as it is conveyed to the outlet of the mixer-extruder;
 (2) incorporating the mixture of emulsifiers in the soft paste obtained in (1); and
 (3) incorporating, with stirring, of the mixture obtained in (2) in the aqueous phase.

21. The process according to claim 20, wherein the stages (2) and (3) are carried out in the screw mixer-extruder of stage (1).

22. A method of treating, protecting, caring for or cleansing the skin, mucous membranes or hair or a combination thereof, which comprises administering an effective amount of the composition of claim 1 to a manual in need thereof.

23. The method of claim 22, wherein said mammal is a human.

24. A method of treating wrinkles or lines in mammalian skin or both, which comprises administering an effective amount of the composition of claim 1 to a mammal in need thereof.

25. The method of claim 24, wherein said mammal is a human.

* * * * *

UNITED STATES PATENT AND TRADEMARK OFFICE
CERTIFICATE OF CORRECTION

PATENT NO.    : 6,488,941 B1
DATED         : December 3, 2002
INVENTOR(S)   : Veronique Burnier et al.

It is certified that error appears in the above-identified patent and that said Letters Patent is hereby corrected as shown below:

Column 9,
Line 32, change "composition" to -- The composition --

Signed and Sealed this

Thirteenth Day of May, 2003

JAMES E. ROGAN
*Director of the United States Patent and Trademark Office*